US009538926B2

(12) United States Patent
Durduran et al.

(10) Patent No.: US 9,538,926 B2
(45) Date of Patent: Jan. 10, 2017

(54) SPECKLE CONTRAST OPTICAL TOMOGRAPHY

(71) Applicants: FUNDACIO INSTITUT DE CIENCIES FOTONIQUES, Castelldefels, Barcelona (ES); WASHINGTON UNIVERSITY, St. Louis, MO (US)

(72) Inventors: Turgut Durduran, Barcelona (ES); Claudia Valdes, Barcelona (ES); Anna Kristoffersen, Barcelona (ES); Hari M. Varma, Barcelona (ES); Joseph Culver, St. Louis, MO (US)

(73) Assignees: FUNDACIO INSTITUT DE CIENCIES FOTONIQUES, Castelldefels, Barcelona (ES); WASHINGTON UNIVERSITY, St. Louis, MO (US)

( * ) Notice: Subject to any disclaimer, the term of this patent is extended or adjusted under 35 U.S.C. 154(b) by 95 days.

(21) Appl. No.: 14/141,227

(22) Filed: Dec. 26, 2013

(65) Prior Publication Data
US 2015/0182136 A1    Jul. 2, 2015

(51) Int. Cl.
| A61B 5/05 | (2006.01) |
| A61B 5/026 | (2006.01) |
| G01B 9/02 | (2006.01) |
| A61B 5/00 | (2006.01) |

(52) U.S. Cl.
CPC .......... *A61B 5/0261* (2013.01); *A61B 5/0062* (2013.01); *A61B 5/0073* (2013.01); *G01B 9/02094* (2013.01); *A61B 5/0066* (2013.01); *A61B 5/7203* (2013.01)

(58) Field of Classification Search
CPC .......................... A61B 5/0261; A61B 5/0073
See application file for complete search history.

(56) References Cited

U.S. PATENT DOCUMENTS

| 7,551,293 B2 * | 6/2009 | Yelin | G01B 9/02027 356/456 |
| 2012/0095354 A1 | 4/2012 | Dunn et al. | |

OTHER PUBLICATIONS

Heng He, et al. "Lateral laser speckle contrast analysis combined with line beam scanning illumination to improve the sampling depth of blood flow imaging" 2012 Optical Society of America, Optics Letters, vol. 37, No. 18, Sep. 15, 2012; pp. 3774-3776.
Guanping Feng, et al. "Laser speckle projection tomography", 2013 Optical Society of America, Optics Letters, vol. 38, No. 15, Aug. 1, 2013, pp. 2654-2656.
Renzhe Bi, et al. "Multi-channel deep tissue flowmetry based on temporal diffuse speckle contrast analysis", Sep. 23, 2013, vol. 21, No. 19, Optics Express 22854.
(Continued)

*Primary Examiner* — Rajeev Siripurapu
(74) *Attorney, Agent, or Firm* — Lucas & Mercanti, LLP

(57) ABSTRACT

Speckle contrast optical tomography system provided with at least one point source and multiple detectors, means for providing different source positions, the point source having a coherence length of at least the source position-detector distance and means for arranging the source position-detector pairs over a sample to be inspected, the system being further provided with means for measuring the speckle contrast; the speckle contrast system of the invention thus capable of obtaining 3D images.

6 Claims, 12 Drawing Sheets

(56) References Cited

OTHER PUBLICATIONS

Renzhe Bi, et al. "Deep tissue flowmetry based on diffuse speckle contrast analysis", May 1, 2013, vol. 38, No. 9, Optics Letters, pp. 1401-1403.
Chao Zhou, et al. "Diffuse optical correlation tomography of cerebral blood flow during cortical spreading depression in rat brain", Feb. 6, 2006, vol. 14, No. 3, Optics Express, pp. 1125-1144.
European Search Report dated Jun. 3, 2015 to corresponding Application No. EP 14 19 9712.
J. David Briers, et al., Laser Speckle Contrast Analysis (LASCA): . . . , Journal of Biomedical Optics, vol. 1, No. 2, pp. 174-179, 1996.
R. Bonner, et al., Model for Laser Doppler Measurements of Blood Flow in Tissue, Applied Optics, vol. 20, No. 12, pp. 2097-2107, 1981.
Vladimir C. Hachinski, MD, FRCP(C), et al., Cerebral Blood Flow in Dementia, Arch Neurol, vol. 32, pp. 632-637, 1975.
J. David Briers, Laser Doppler, Speckle and Related Techniques . . . , Institute of Physics Publishing, Physiol. Meas., vol. 22, pp. R35-R66, 2001.
N. Schuff, et al., Cerebral Blood Flow in Ischemic Vascular . . . , NIH Public Access, Author manuscript; available in PMC Nov. 1, 2010, pp. 1-15.

\* cited by examiner

SPECKLE CONTRAST OPTICAL TOMOGRAPHY

BACKGROUND OF THE INVENTION

The present invention is related to subsurface tissue blood flow imaging techniques. More particularly, the invention is based on a new highly efficient technique based on coherent laser light speckle contrast (SC) and diffuse correlation tomography.

Imaging blood flow is critical to the diagnosis and monitoring of many diseases. Examples include most obviously the imaging of cerebral blood flow (CBF) for stroke and other ischemic injuries—all hemodynamic derangements—and also neurodegenerative diseases such as Alzheimer's.

Coherence optical measures have traditionally had a role in rodent stroke studies by way of the laser Doppler flowmetry point measurement technique. Areas of high blood flow increase the Doppler broadening of coherent laser light. However, laser Doppler methods are point measures that rely on single scattering with limited depth penetration (<1 mm). Laser Doppler methods can be extended to imaging by raster scanning the Laser Doppler probe, but this is very slow.

Speckle methods monitor blood movement through measures like the speckle contrast related to the intensity autocorrelation function, $C(\tau)$, of coherent laser speckle. The speckle contrast will decay more quickly in tissue with faster blood flow.

There are three distinct speckle measurement approaches including: spectral (laser Doppler, LD) temporal (correlation spectroscopy) and spatial (speckle contrast). Traditional LD analysis monitors the C(T) by looking at Doppler broadening of speckle in the light frequency domain. Spatial methods monitor an integrated measure, by temporally integrating the intensity of many spatially distinct speckles for a fixed time (with a CCD for example) and performing a spatial statistical analysis.

In US 2012/0095354 Dunn et al describes laser speckle contrast imaging. However Dunn et al. presents many limitations, like noise, and is not suitable for 3D imaging.

SUMMARY OF THE INVENTION

The present invention extends high speed speckle contrast measurements to deep tissue, three-dimensional imaging. It addresses the previous weaknesses of optical correlation methods and provides high number of low cost, speckle measurements for three dimensional imaging of blood flow in preclinical and human imaging. The advantages of the invention are the cost effectiveness of speckle detection simplicity and high speed (>100 kHz—per source-detector pair measurement), and potential high sensitivity through use of many speckle measurements. The speckle contrast optical tomography (SCOT) system of the invention is provided with at least one point source and multiple detectors, means for providing different source positions, the point source having a coherence length of at least the source position-detector distance and means for arranging the source position-detector pairs over a sample to be inspected, the system being further provided with means for measuring the speckle contrast.

BRIEF DESCRIPTION OF THE DRAWINGS

To complete the description and in order to provide for a better understanding of the invention, a set of drawings is provided. Said drawings illustrate a preferred embodiment of the invention, which should not be interpreted as restricting the scope of the invention, but just as an example of how the invention can be embodied.

DETAILED DESCRIPTION OF THE INVENTION

For the method of the invention, measurements at multiple detectors from more than one source position are needed. This can be done in following ways:

If x source positions are needed, the source has to be scanned through the sample in x different locations. This can be made by different approaches:

(A) Arrange x separate laser sources in such a way to illuminate on the x different scanning locations we need to have. Now switch ON each of the x lasers one at a time and record the corresponding measurements.

(B) Use only one laser source but couple this laser light into x different optical fibres and arrange each of the optical fibres in x different scanning locations on the sample. The laser light must come out from one fibre at a time; for this an optical switch can be used. By controlling the optical switch the laser source can be coupled to each fibre one at a time.

(C) Use only one laser source, employing a galvo mirror arrangement controlled by a computer to achieve x different locations. The preferred embodiment is the method C.

Figure 1:
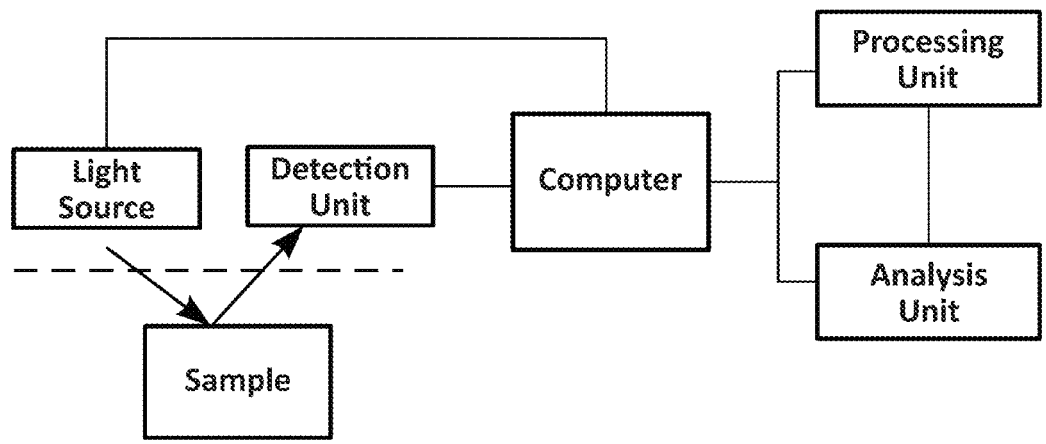
FIG. 1 is a block diagram of the system of the invention.
Figure 2:
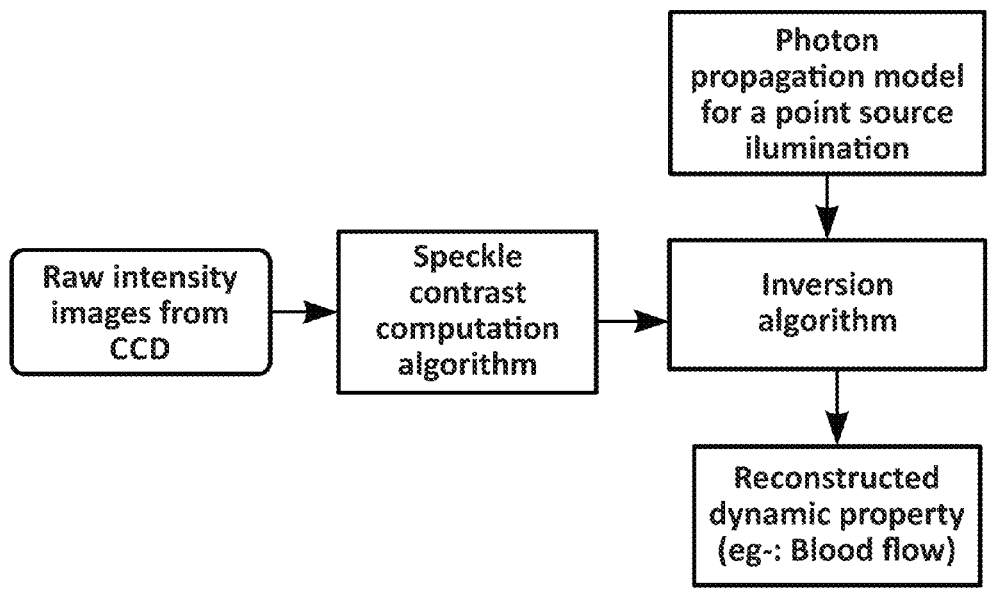
FIG. 2 is a flowchart of the process of the invention when applying the system described in FIG. 1.

For the preferred embodiment, the optical instrumentation needed comprises:

A coherent light source, a focusing lens to make a point source, a detection unit, for example, a CCD, CMOS or SPAD array with objective lens, data acquisition and processing unit for acquiring raw intensity images and processing speckle contrast data. The block diagram in FIG. 1 depicts the SCOT system. The method developed for the reconstruction of flow to be used in conjunction with the optical instrumentation for SCOT is explained in FIG. 2.

Multiple sources and detectors are arranged so as to sample the tissue surface over the tissue volume of interest. The light source is a point source, for example a focused or fiber guided laser that can be modeled as a point source at the surface of the sample according to the photon diffusion model. That is, the source can be considered as a point source after traveling a distance of 1* inside the turbid media, where 1* is the mean scattering length. For our purpose, the diameter of the source should be much smaller than the source-detector distance, rd, typically less than 100 microns. The source is a continuous wave meaning that it should be continuous during a time approximately equal to or longer than the exposure time of the detection system. The coherence length should be larger than all the photon pathlengths in the turbid media. The minimum coherence length should be equal to rd, but typically is around 10 m. The multiple source positions can be achieved by scanning one point source, e.g. using galvanometric mirrors or by using multiple point sources switching on one at a time. The different source positions do not need to be coherent with each other since the interference patterns are measured separately for each source illumination position.

To detect the transmitted or reflected light the invention comprises at least one aperture and a detector array. The aperture can be an adjustable magnification objective. Examples of suitable detectors are CCD cameras, sCMOS cameras, arrays of photon counting detectors or SPADs. The distance from the point source to the detectors, rd, should be larger than 3 1*.

Detectors should also allow the control and/or the variation of the exposure time in the data acquisition in a range where the lower limit is defined by signal to noise ratio (SNR) greater than 1 and the upper limit is determined when the calculated speckle contrast is smaller than the shot noise of the pixel measurements.

The SC data may be corrected for intensity gradients and for shot noise errors that would otherwise corrupt the pattern of SC and corrupt the imaging. Specifically, the data can be corrected for shot noise using a mathematical model based on Poisson statistics. Specifically, a corrected speckle contrast measure can be created that is equal to the square root of the square of the raw speckle contrast minus the square of the shot noise (computed using the Poisson statistics model) before proceeding to tomography. Further, for intensity gradient correction with in the region of interest (ROI), a theoretical model for intensity based on diffusion equation is computed and then divide the raw intensity at each pixel by the theoretical/fitted intensity.

Figure 3:
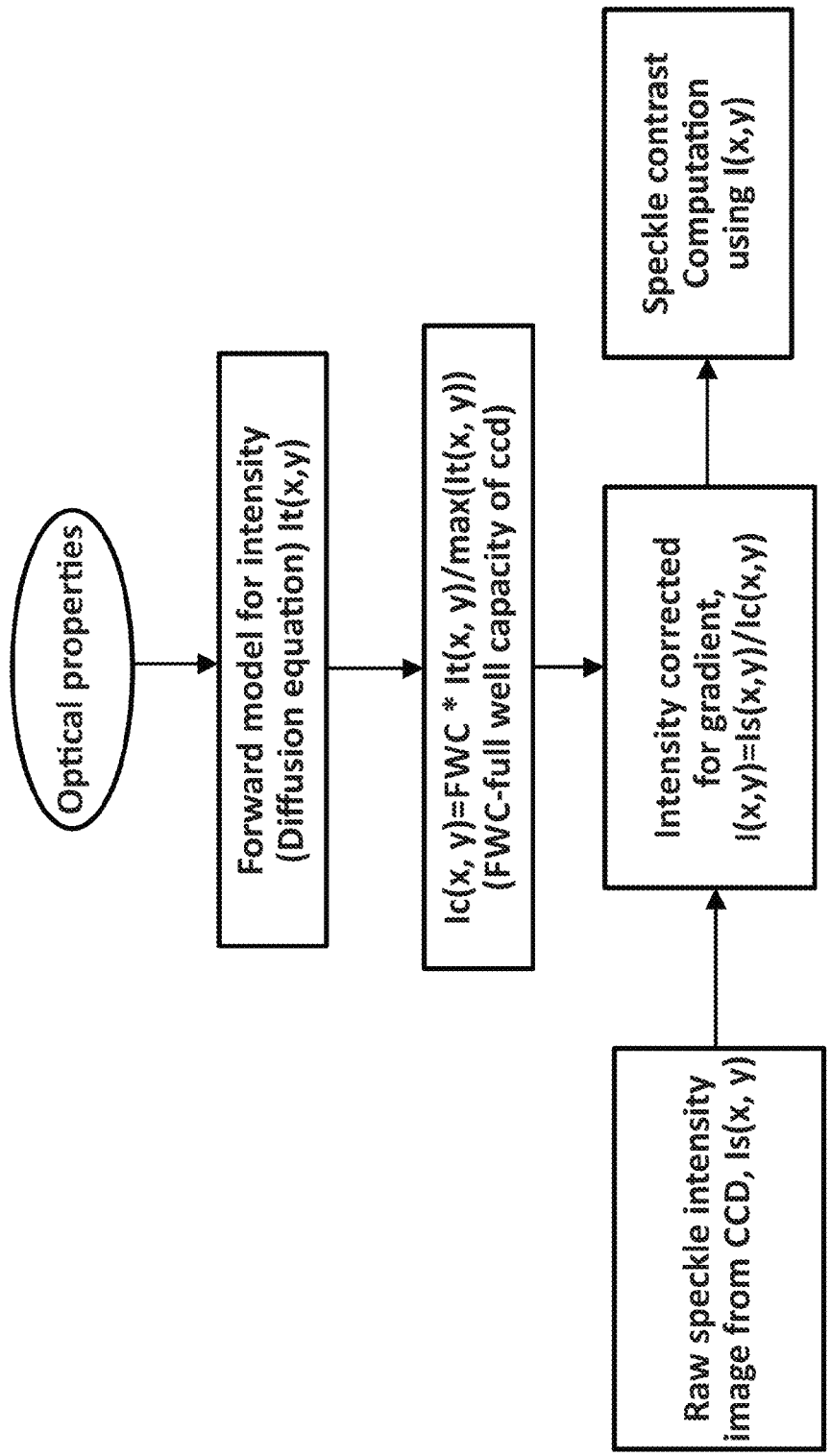
FIG. 3 shows the block diagram describing the correction procedure for intensity gradients in the measured raw intensity images.

This removes the variance in the speckle values due to the intensity gradient. A block diagram showing the correction procedure for intensity gradients is shown in FIG. 3.

Figure 4:
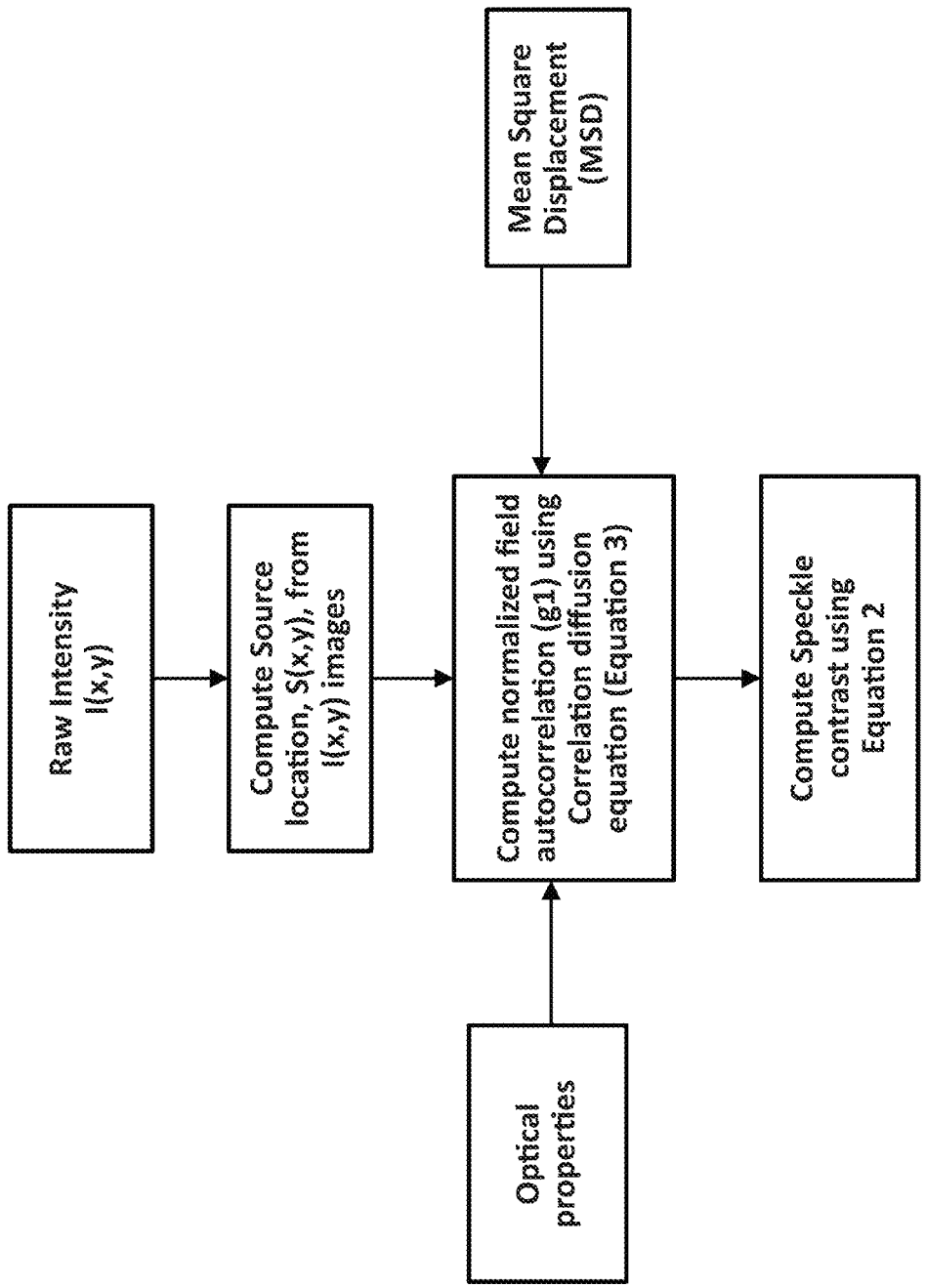
FIG. 4: describes the forward model for the SCOT based on correlation diffusion equation.

A SC forward model (as shown in the block diagram in FIG. 4) for the imaging array and the tissue volume is constructed for SC contrasts that predicts SC measurements for hypothetical flow images.

The SC data is inverted, using the SC forward model, to generate images of flow.

In Detail:
1. Measurements of speckle contrast are made between a plurality of source and detector pairs that transverse a tissue volume. The detectors each consists of a region of multiple pixel samplings of speckles. In one embodiment, a lens relays the speckle pattern from a tissue surface to a CCD camera. The field of view of the camera (e.g. 512×512 pixels) is decimated into a grid of 7×7 pixel regions. Each 7×7 is a SC detector, where the speckle contrast (K) is calculated as the standard deviation of the full 49 pixels—divided by—the mean value of the full 49 pixels as, $$K = \frac{\sigma}{\mu},$$ Equation 1 intensity computed in the 7×7 window.

The light detection is integrated over a defined exposure time. In the simplest version the exposure time is the same for all detectors and sources. In another embodiment, exposure time scenarios, including multiple exposure times can be used to optimize the signal to noise ratio of each measurement.

Figure 5:
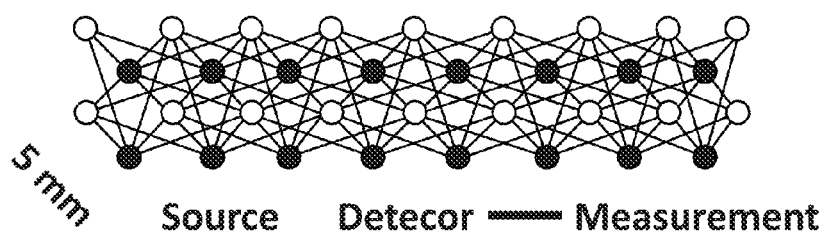
FIG. 5: shows the arrangement of sources and the detectors in a rectangular grid array.
Figure 6A:
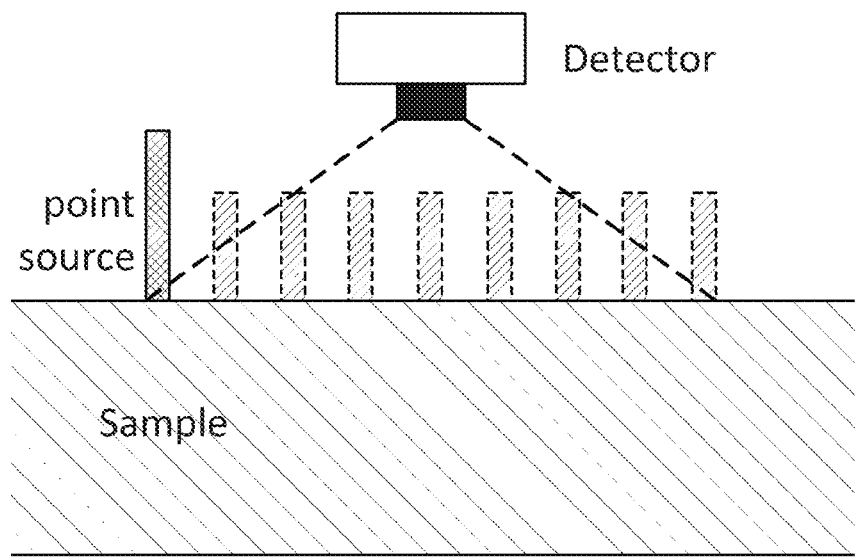
FIGS. 6a and 6b: describe two possible configurations of the invention, in reflection and transmission geometries, respectively.

2. The arrangement of the sources and detectors samples the tissue surface over the tissue volume of interest, with multiple source-detector pair distances and overlapping measurement volumes (see FIG. 5). Two possible geometries include reflectance and transmission. In reflectance (see FIG. 6a) the sources and detectors are on the same side of the sample. In the transmission geometry (see FIG. 6b), the sources are on one side of the sample, and the detectors are on the other side. In each case a simple sampling pattern is a rectangular evenly spaced grid. For instance if the sample is 1 cm thick, and the volume interest is 3.2 cm×3.2 cm by 1 cm, then a 32×32 array of source positions would illuminate one side of the sample. A similar 32×32 array of detectors would be constructed from a CCD image of the opposite side of the sample. Each source would be paired with each detector to construct a full measurement list of each source detector grid. For each source-detector measurement, the speckle contrast is computed for each assigned exposure time. More complex source-detector geometries can be constructed in which a flexible mesh of sources is interpolated within a flexible mesh of detectors to cover and arbitrary tissue volume (for example see arrangement for a human head in FIG. 7).

3. The data is corrected for homogeneous gradients and shot-noise (explained in the following). A forward model relating speckle contrast to medium flow profile based on field autocorrelation function is given as $$K = \frac{2\beta}{T} \int_0^T g_1^2(r, \tau)\left(1 - \frac{\tau}{T}\right) d\tau$$ Equation 2

Where $g_1(r, \tau)$ is the field autocorrelation function, $\tau$ is the correlation time, T is the exposure time of the detector array, and $\beta$ is 0.5

Unlike the case of laser speckle contrast imaging with uniform source illumination where the field autocorrelation depends only on correlation time, $\tau$, $g_1$, in the case of SCOT, it depends also on the spatial co-ordinate r as given by the correlation diffusion equation (CDE):

$$-\nabla \cdot D \nabla G(r, T) + (\mu_a + \frac{1}{3}(\mu_s k_0)^2 <\Delta r^2(r,\tau)>) G(r, T) = q_0(r)$$ Equation 3

Where $G(r,\tau)$ is the un-normalized field autocorrelation which is related to $g_1$ As $$g_1(r, \tau) = \frac{G(r, \tau)}{G(r, 0)}.$$

Here $D$, $\mu_a$, $\mu_s'$, and $k_0$ are diffusion coefficient, absorption coefficient, reduced scattering coefficient and magnitude of wave vector respectively. The laser point source is represented by $q_0(r)$ where r is the spatial co-ordinates.

The term $<\Delta r^2(r,T)>$ is called the mean square displacement which models the Brownian motion as well as the random flow given by $6D_B\tau$ and $V^2\tau^2$ respectively. Here $D_B$ is called particle diffusion coefficient (in cm$^2$/sec) and V is the random flow with unit of velocity. The relation connecting source-detector (representing the flow) to field autocorrelation as given in Equation 3 along with the expression for speckle contrast K in terms of $g_1$, as given in Equation 2, constitutes the forward model for SCOT.

Note that the diffusion equation used for correcting intensity gradient is different from the CDE in Equation 3. CDE can be reduced to diffusion equation for intensity by substituting MSD=0 which gives $l(r)=G(r,0)$.

4. The forward model is used to compute SC for each source-detector pair. The data corrected for the natural gradient in light intensity by normalizing the data within the speckle region of interest.

The measured speckle contrast is corrected for shot noise ($K_c$) using the equation:

$$K_c = \sqrt{K^2 - K_s^2} \qquad \text{Equation 4}$$

Here K is the SC measured from raw intensity images and $K_s$ is the speckle contrast due to shot noise given by $$K_s = \frac{1}{\sqrt{\mu}}$$

which is based on Poisson statistics model for shot noise.

5. A SC forward model (Equations 2 and 3) for the imaging array and the tissue volume is constructed for SC contrasts. To reconstruct the three dimensional distribution of flow, $\Delta V$ a differential forward model that predicts differential SC contrasts for arbitrary hypothetical flow contrasts is derived based on first Born approximation:

$$K_c^2 - K_{co}^2 = \frac{-4\beta}{T} \int_0^T c_v \tau^2 \left(1 - \frac{\tau}{T}\right) \qquad \text{Equation 5}$$
$$\frac{g_1^0(r, \tau)}{G(r, 0)} \left[\int G(r', r_d, \tau) G_1^0(r', r_s, \tau) \Delta V^2 dr'\right] d\tau$$

Where $K_{co}$ is the baseline SC corresponding to case from which the flow contrast is to be measured. The baseline is defined as the SC measurement made on a tissue at resting or reference state or on a tissue simulating phantom. The change in SC from $K_{co}$ to $K_c$ can be due to flow contrast induced by an externally applied stimulus. The stimulus [6,7] can be neural (eg:. stimulating the forepaw), Pharmacological (eg: Drug-induced stimulus) and physiological (Eg: tilting the head etc.). The contrast in SC can also be due to the flow contrast in some part of the tissue compared to the rest due to a physiological change induced by diseases like cancer etc.

Here $g_1^0$ and $G_1^0$ corresponds to rest/reference state of the tissue and $c_v = \frac{1}{3}(\mu_s \cdot k_0)^2$. The spatial co-ordinates of the sources and detectors are denoted by $r_s$ and $r_d$ respectively. The differential forward model is derived from the forward model (comprising Equations 2 and 3) by expanding the SC in Taylor's series as a function of flow and then truncating the second and higher order differentials, which is precisely the first Born approximation.

6. The source-detector measurement data is reconstructed into an image of flow. The inverse problem (based on Equation 5) is solved to estimate the flow contrasts, $\Delta V$, from the measured source-detector pair SC contrast (left hand side of Equation 5). Equation 5 is discretized in the source-detector geometry shown in FIG. 5a to get a linear system of equations, Y=AX, where $Y=K_c^2-K_{co}^2$, A is called the Jacobian matrix evaluated using the integral in right hand side of Equation 5 and $X=\Delta V$ is the flow contrast to be determined. The solution of this linear system of equations gives the flow contrast $\Delta V$. Here we adopt the standard regularization procedures reported in the context of optical tomography to solve the 7. the linear system of equations [6,8,9].

The speckle contrast forward model in step 3 comprises the calculation of the speckle contrast with spatial or temporal statistics. Unlike traditional SC, the method of the invention uses a model for the propagation of speckle contrast through tissue. As photons propagate through the tissue, they are multiply scattered and absorbed and this is, generally, described by the photon diffusion model. If the scatterers, namely red blood cells, are in motion then the diffused light and the resultant speckles fluctuate. The statistics of these fluctuations can be described by a photon diffusion model for temporal autocorrelation functions, which is the correlation diffusion equation (CDE) given in Equation 3. SC is the integral of this function as shown in Equation 2. The forward model takes the dynamics of the red blood cells ("blood flow" which is modeled as mean square displacement), the absorption and scattering properties, their heterogeneities and the boundaries around the tissues to predict the measured SC. Then, the forward model is inverted. The data can be inverted using techniques developed for diffuse optical tomography, optimized against the noise present in SC data sets. There are two basic approaches: either iterative inversion or direct inversion. With iterative inversion each source-detector pair or group of data are projected through the use of the forward model onto an estimated image, step by step, iterating across different measurements. With a direct inversion approach, the forward model matrix is directly inverted numerically, and the image reconstruction is accomplished in a single matrix multiplication of the inverted sensitivity matrix times the SC data. The sensitivity matrix can be computed using the differential forward model given in Equation 5.

A specific example according to the above preferred embodiment of the present invention, can be effectively employed to recover the three dimensional flow distribution embedded inside a tissue phantom.

Figure 8:
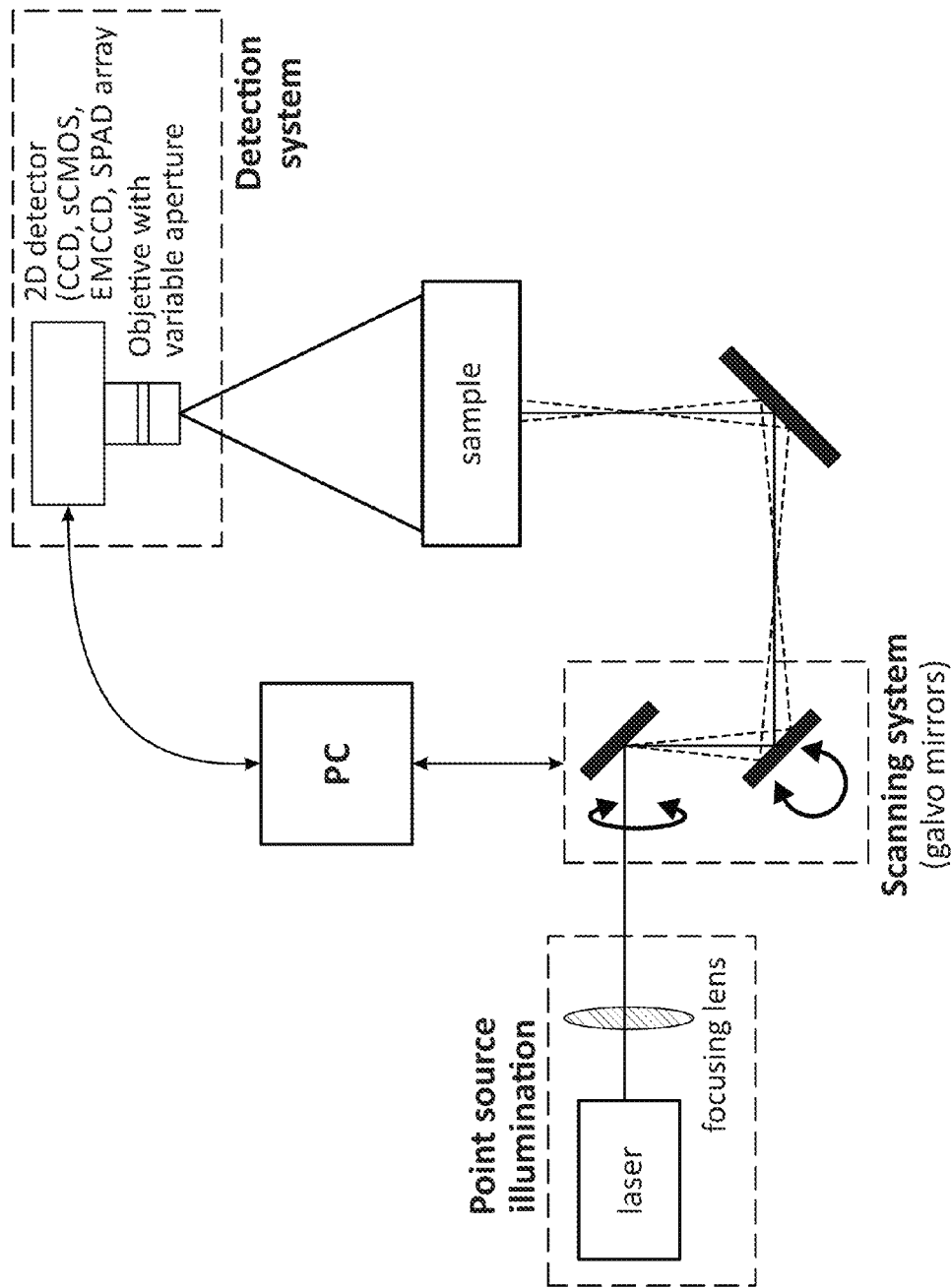
FIG. 8 shows the experimental arrangement of SCOT.

The SCOT experimental apparatus is depicted in FIG. 8 where a liquid phantom having same optical and dynamical properties as that of the biological tissue as the sample is used.

Specifically, a transparent plastic container of size 3.8 cm×1.5 cm×5 cm is filled with 1% Lipofundin® MCT/LCT solution in water resulting in a phantom with $\mu_a$=0.026 cm$^{-1}$, $\mu_s$=10 cm$^{-1}$ and $$D_B = 9.9 \times \frac{10^{-9} \text{cm}^2}{\text{sec}}.$$

Figure 6B:
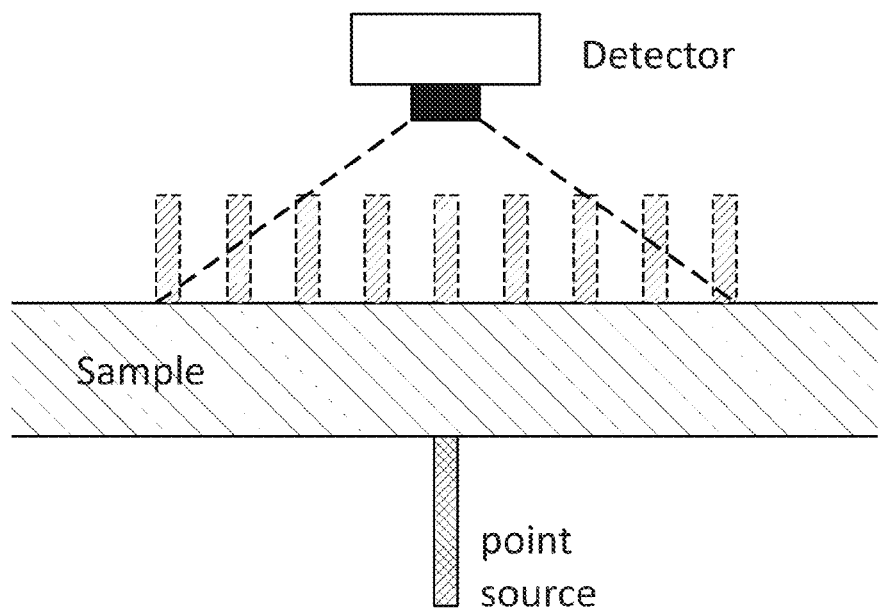
Figure 7:
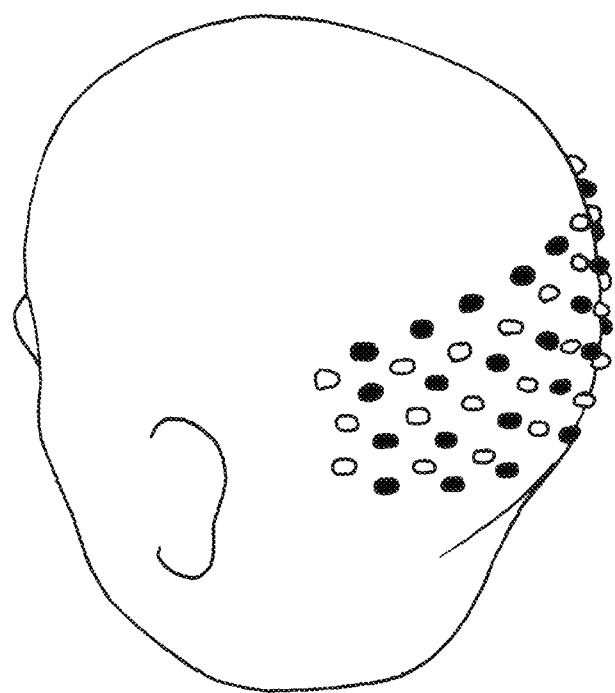
FIG. 7: shows the source detector arrangement for SCOT in a human head model.

A temperature controlled continuous laser diode (Thorlabs L785P090, 785 nm, 90 mW) is focused down to a beam of 1 mm diameter to probe the sample. The transmission geometry as shown in FIG. 6(b) is used, where the light source is focused on the bottom of the sample and the produced speckle patterns were imaged from the top with a camera (sCMOS; Orca ash4.0, Hamamatsu).

A f-number of 16 is set in the objective lens of the camera to match the speckle size to pixel size. The exposure time, T, of the camera was set to 1 ms. A tube of 0.4 cm diameter is introduced inside the rectangular container through which the same liquid phantom is pumped using a peristaltic pump with the following velocities:

(0.11,0.21,0.32,0.43,0.64,0.85,1.06,2.12,3.18) cm/sec.

Using the galvo-mirror unit the source is scanned in three rows each having 25 source positions. The laser is set in every position during 0.5 seconds to acquire 35 intensity images per source, with a 1 ms exposure time and for each velocities, the transmitted intensity images are recorded. For each source in the image, 300 detectors are defined, located at XZ plane for Y=1.5 cm (25 detectors in each of the 12 lines) thus comprising a total of 22500 source-detector pairs which serves as the SCOT data. For each detector position, a 5×5 pixel window is considered for which the intensity gradient corrections are applied and subsequently the mean and the standard deviation of intensities in those 25 pixels are calculated. These values are averaged over time (frames) for all the images corresponding to each source and using Equation 1 the speckle contrast for each detector is computed. Finally using the Equation 4, the SC is corrected for shot noise ($K_c$).

Figure 9:
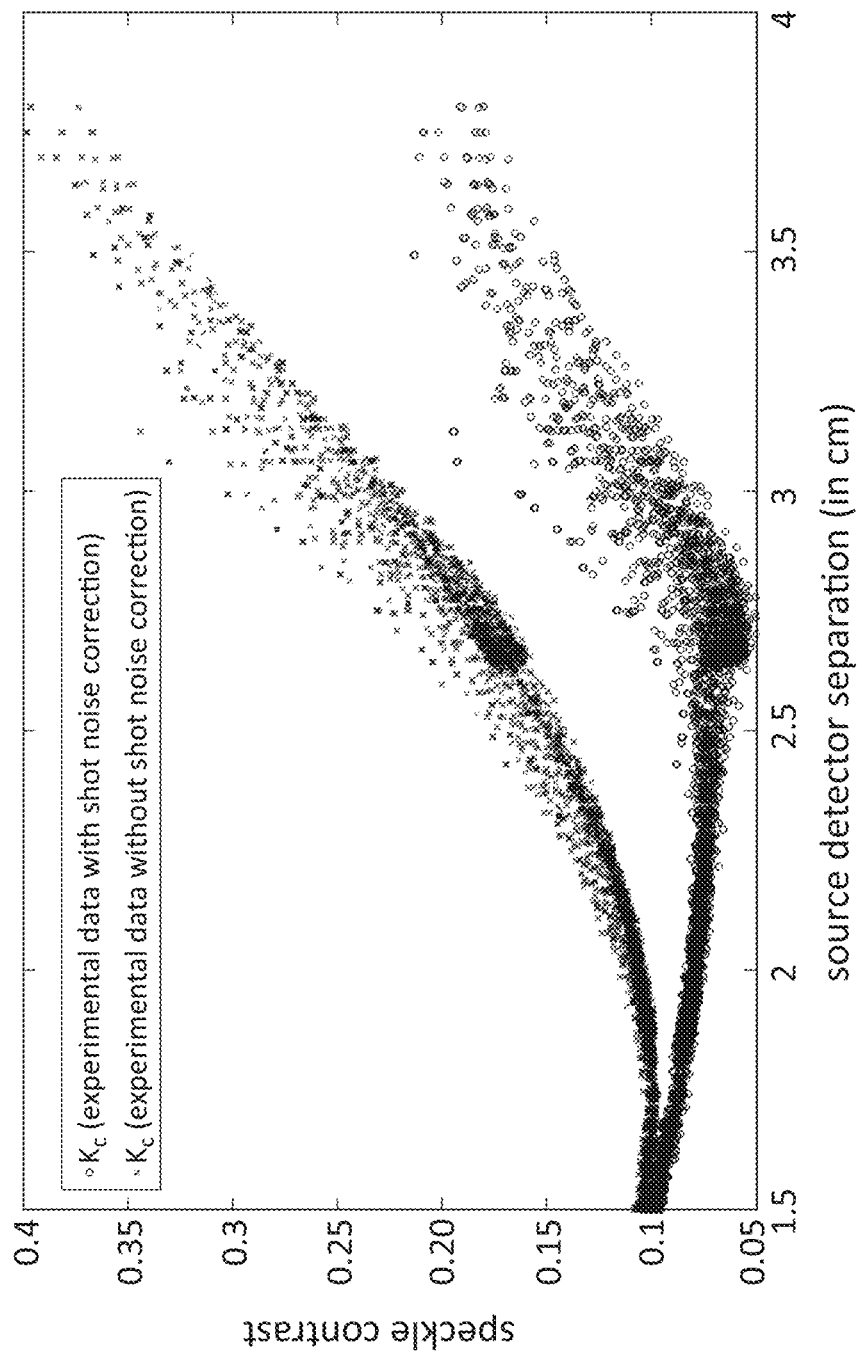
FIG. 9: plots speckle contrast as a function of source detector separation for two cases: $K_C$ is the SC with shot noise correction computed using Equation 4 and K is SC without shot noise correction. Both are computed from experimental raw intensity images acquired from Lipofundin phantom.

FIG. 9 shows speckle contrast as a function of source detector separation where $K_c$ is the baseline SC with shot noise correction computed using Equation 4 and K is SC without shot noise correction. The baseline SC is computed from raw speckle intensity images acquired using the above mentioned experiment on Lipofundin® phantoms.

We would like to briefly explain the need of baseline SC measurement in the medium. The method of tomographic reconstruction has two parts 1) to measure a baseline data and 2) based on above measured baseline data, reconstruct the quantity of interest. Aim of SCOT is to reconstruct the flow contrast from the baseline scenario . So first acquire the baseline measurement. Then introduce the stimulus which will alter the flow in one or more spatial locations in the medium and acquire another set of speckle contrast measurement. Then use the above two sets of data to reconstruct the flow distribution.

For this particular experiment to demonstrate one of the several applications of the present invention, we chose the baseline to be the SC measurement in the absence of flow. The stimulus in this case is the peristaltic pump which will introduce the flow to the system. In FIG. 9 we have shown SC for baseline measurement only in order to show the effect of shot noise and the correction procedure.

In order to apply differential model in Equation 5 to reconstruct the flow from $K_c$, the background SC in the absence of flow ($K_{co}$) has to be determined.

The experimentally determined $K_c$, is fitted against the K obtained using the forward model (Equations 2 and 3) for different $D_B$ values using nonlinear least square fitting algorithm. The experimentally measured values of optical absorption ($\mu_a$=0.026 cm$^{-1}$) and the scattering coefficient ($\mu_s$=10 cm$^{-1}$) were used for the fitting algorithm which gives $D_B$=1.86×10$^{-8}$cm$^2$/sec whereas the experimentally determined (using diffuse correlation spectroscopy, DCS) $D_B$ has a value of 0.92×10$^{-8}$cm$^2$/sec. From this fitted $D_B$, $K_{co}$ is determined using the forward model.

Equation 5 is discretized in the rectangular grid geometry shown in FIG. 5(a) to get a matrix equation which is solved for flow velocity V.

Figure 10A:
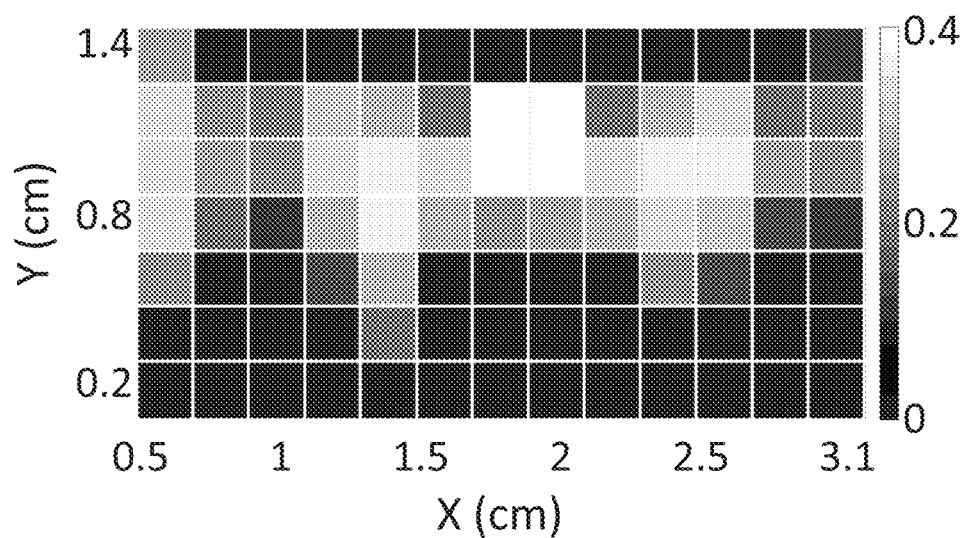
FIG. 10: (a) Reconstructed distribution of flow velocity (in cm/sec) in the XY plane using SCOT, (b) the original distribution of flow velocity in XY plane.
Figure 10B:
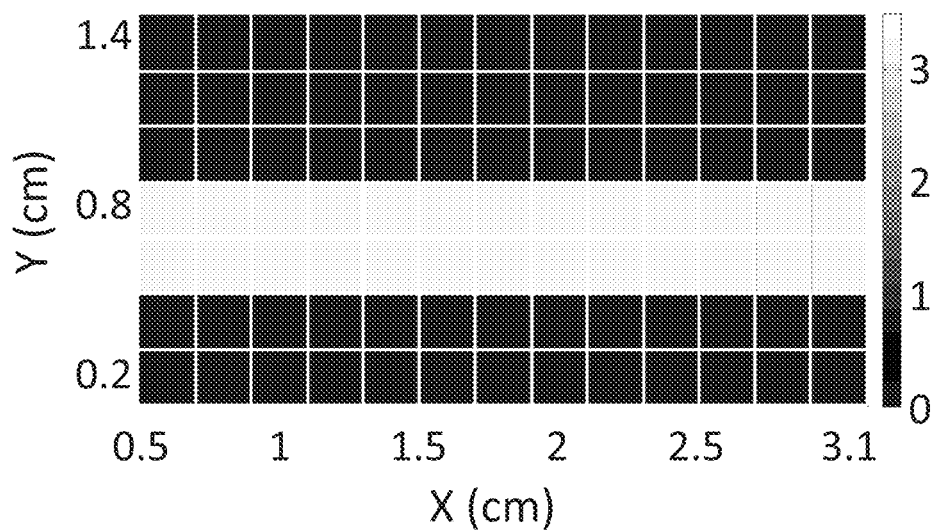
Figure 11A:
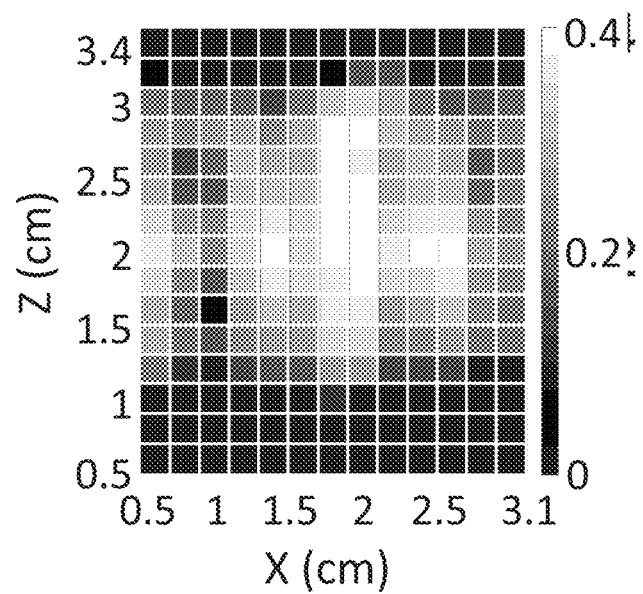
FIG. 11:(a) Reconstructed distribution of flow velocity (in cm/sec) in the XZ plane using SCOT, (b) the original distribution of flow velocity in XZ plane.
Figure 11B:
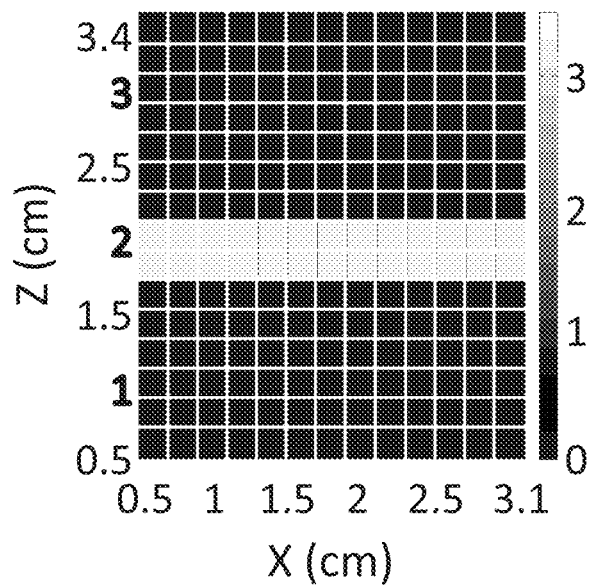
Figure 12A:
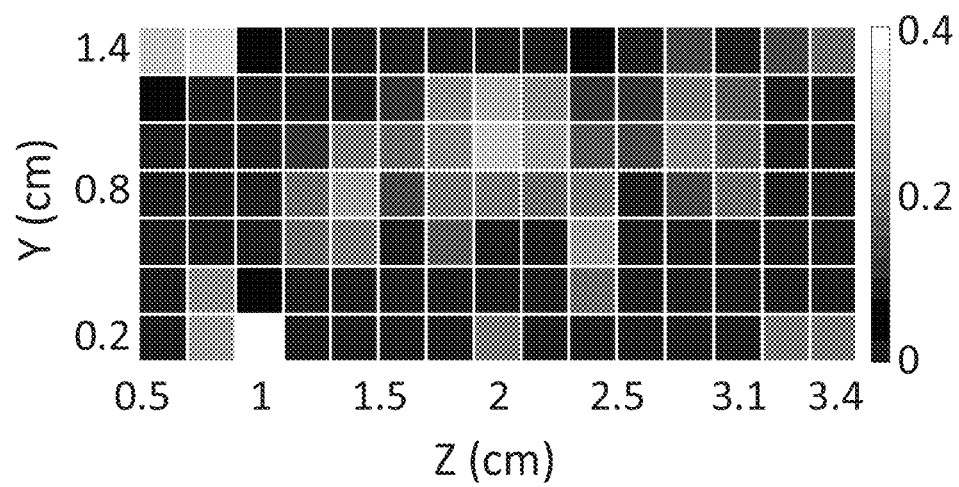
FIG. 12: (a) Reconstructed distribution of flow velocity (in cm/sec) in the YZ plane using SCOT, (b) the original distribution of flow velocity in YZ plane.
Figure 12B:
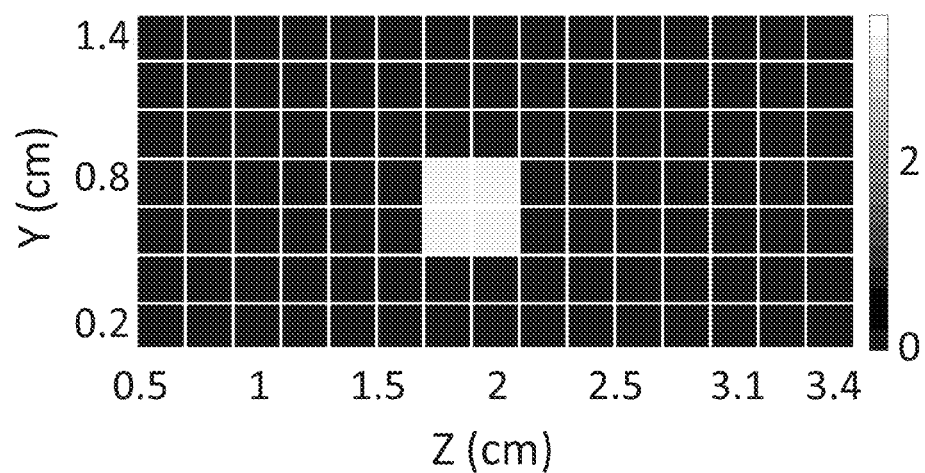
Figure 13:
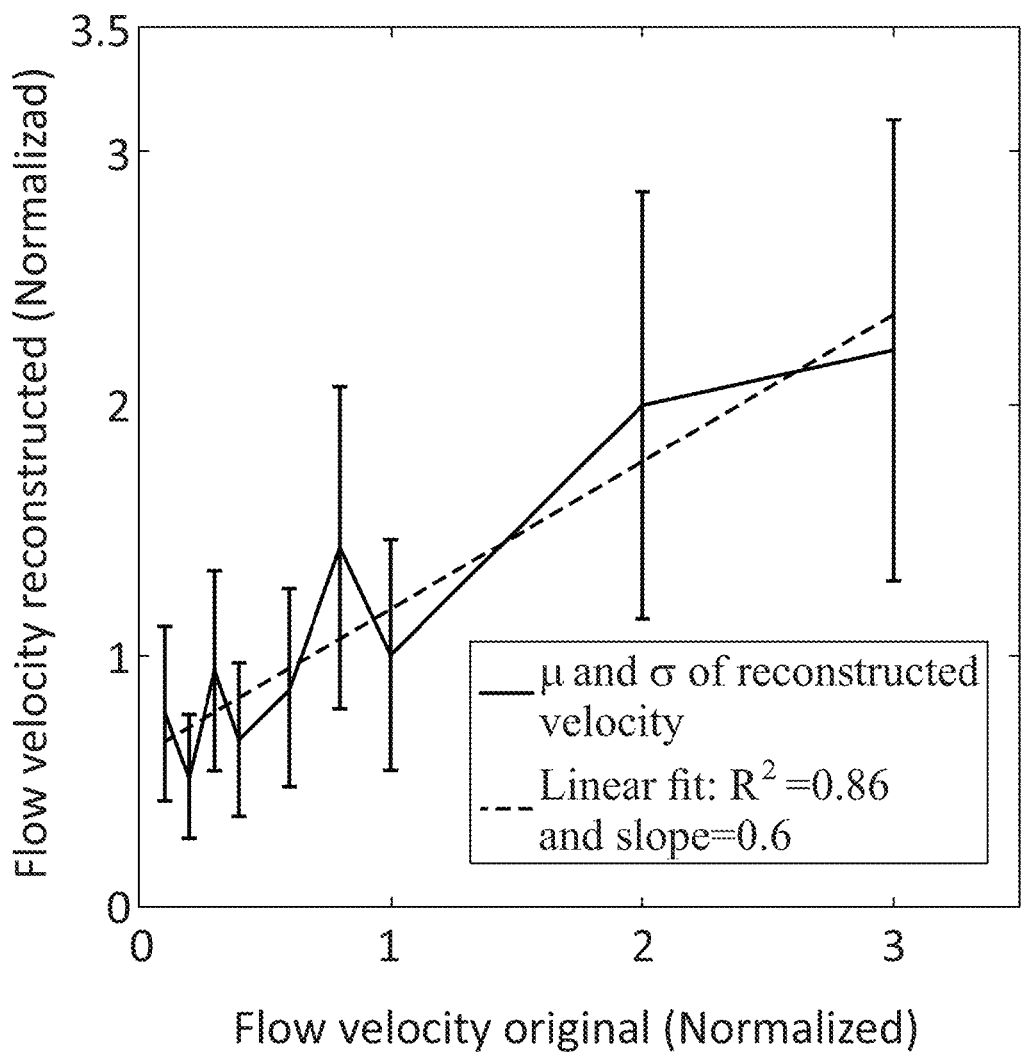
FIG. 13: The reconstructed normalized flow is plotted against the normalized original flow.

The distribution of reconstructed and original V in the XY plane is shown in FIGS. 10(a) and 10(b) respectively. The original velocity distribution in XY plane as shown in FIG. 10(b) shows the presence of a flow represented by the brighter region of the plot whereas the darker region indicates the absence of the flow. The reconstructed velocity distribution using the SC obtained from a sample, containing the original velocity distribution as shown in FIG. 10(b), is shown in FIG. 10(a). The reconstructed plot in FIG. 10(a) contains grey levels in between the brighter (high velocity flow) and darker regions (absence of flow) which shows that the reconstructed velocity is not exact but a distributed representation of the original velocity which is quite common in these type of nonlinear inverse problems. The maximum value of the reconstructed velocity is approximately one seventh of the maximum value of the original velocity. Similar plots for XZ and YZ planes are shown in FIGS. 11 and 12 respectively. The reconstructed normalized flow is plotted against the normalized original flow as shown in FIG. 13. These reconstructed flow values are obtained by averaging the reconstructed flow velocity in predetermined area (matching the original position of the tube) defined on the YZ planes. The standard deviation of the reconstructed flow in this region is also shown in the same figure. The normalization is done by dividing the original and reconstructed flow corresponding to the flow value of 1.0616 cm/sec. A linear fit of the reconstructed flow gives a slope of 0.6 showing that the Born approximation under estimate the original flow value by approximately 40%.

The invention has clear utility in preclinical studies of rodents. It may also have application in humans, either intra-operatively or possibly non-invasively.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A speckle contrast optical tomography system comprising:
   a plurality of point sources each adapted to generate light, each of the plurality of point sources located at a respective first location over a sample to be examined;
   a plurality of detectors located at respective second locations relative to the sample; and
   wherein the plurality of point sources and the plurality of detectors are arranged over a tissue volume of the sample in an arrangement that defines a plurality of source position-detector pairs adapted to examine the tissue volume;
   the speckle contrast optical tomography system further comprising:
   a processing device adapted to:
      determine a speckle contrast between each of the plurality of source position-detector pairs, after light transverses the tissue volume, both in the absence of flow and in the presence of flow, thereby generating speckle contrast data;
      correct the speckle contrast data for shot-noise error and intensity gradients; and
      construct a speckle contrast forward model by performing the following steps:
         computing a field autocorrelation for the plurality of source positions and the plurality of detectors;
         computing the speckle contrast for the plurality of source positions and the plurality of detectors;
         computing a difference value defining a relationship between the speckle contrast corrected for shot noise and intensity gradients and a baseline speckle contrast measurement value; and
         determining a linear system of equations having a solution that provides a flow contrast, based at least in part on the difference value.

2. The speckle contrast optical tomography system of claim 1, wherein:
   the field autocorrelation for the plurality of point sources and the plurality of detectors is computed using a first equation, the first equation being defined as follows:

$-\nabla \cdot D \nabla G(r,\tau) + (\mu_a + \frac{1}{3}(\mu_s k_0)^2 <\Delta r^2(r,\tau)>) G(r,\tau) = q_0(r)$ wherein
   $G(r,\tau)$ is an un-normalized field autocorrelation,
   D, $\mu_a$, $\mu_{s'}$, and $k_0$ are a diffusion coefficient, an absorption coefficient, a reduced scattering coefficient and a magnitude of wave vector, respectively;
   $g_0(r)$ is a respective first location of a point source, wherein r is a set of spatial co-ordinates;
   $<\Delta r^2(r,\tau)>$ is a mean square displacement which models Brownian motion as well as a random flow given by $6 D_B \tau$ and $V^2 \tau^2$, respectively;
   $D_B$ is a particle diffusion coefficient in cm²/sec; and
   V is a random flow with a unit of velocity;
   the speckle contrast for the plurality of point sources and the plurality of detectors is computed based on the computed field autocorrelation and a second equation defined as follows:

$$K = \frac{2\beta}{T} \int_0^T g_1^2(r, \tau)\left(1 - \frac{\tau}{T}\right) d\tau$$

wherein $g_1(r, \tau) = \frac{G(r, \tau)}{G(r, 0)}$ is a normalized field autocorrelation;
   $\tau$ is a correlation time;
   T is an exposure time of a detector array; and
   $\beta$ is 0.5; and
   the difference value indicating the relationship between the speckle contrast corrected for shot noise and integrity gradients and the baseline speckle contrast measurement value is computed using a third equation defined as follows:

$$K_c^2 - K_{co}^2 = \frac{-4\beta}{T} \int_0^T c_v \tau^2 \left(1 - \frac{\tau}{T}\right) \frac{g_1^0(r, \tau)}{G(r, 0)} \left[ \int G(r', r_d, \tau) G_1^0(r', r_s, \tau) \Delta V^2 dr' \right] d\tau$$

wherein
   $K_c$ is the speckle contrast corrected for shot noise and intensity gradients;
   $r_s$ and $r_d$ are spatial coordinates of the plurality of point sources and the plurality of detectors, respectively;
   $K_{co}$ is the baseline speckle contrast value;
   $g_1^0$ and $G_1^0$ correspond to a baseline situation; and
   $C_v = \frac{1}{3}(\mu_s k_0)^2;$ and
   wherein the third equation is discretized in a source-detector geometry to obtain a linear system of equations whose solution provides a flow contrast $\Delta V^2$.

3. A speckle contrast optical tomography system comprising:
   a laser point source adapted to generate light;
   a plurality of detectors arranged over a sample to be examined; and
   a plurality of galvanometric mirrors adapted to provide a plurality of source positions for scanning the source over the sample;
   wherein the plurality of galvanometric mirrors and the plurality of detectors are arranged over a tissue volume of the sample in an arrangement that defines a plurality of source position-detector pairs adapted to examine the tissue volume;
   wherein the laser point source has a coherence length of at least a source position-detector distance;
   the speckle contrast optical tomography system further comprising:
   a processing device adapted to:
      determine a speckle contrast between each of the plurality of source position-detector pairs, after light transverses the tissue volume, both in the absence of flow and in the presence of flow, thereby generating speckle contrast data;
      correct the speckle contrast data for shot-noise error and intensity gradients; and
      construct a speckle contrast forward model by performing the following steps:
         computing a field autocorrelation for the plurality of source positions and the plurality of detectors;
         computing the speckle contrast for the plurality of source positions and the plurality of detectors;
         computing a difference value defining a relationship between the speckle contrast corrected for shot noise and intensity gradients and a baseline speckle contrast measurement value; and
         determining a linear system of equations having a solution that provides a flow contrast, based at least in part on the difference value.

4. The speckle contrast optical tomography system of claim 3, wherein:
the field autocorrelation for the plurality of source positions and the plurality of detectors is computed using a first equation, the first equation being defined as follows:

$$-\nabla \cdot D \nabla G(r,\tau) + (\mu_a + \tfrac{1}{3}(\mu_s k_0)^2 <\Delta r^2(r,\tau)>) G(r,\tau) = q_0(r)$$

wherein
G(r,τ) is an un-normalized field autocorrelation,
D, $\mu_a$, $\mu_{s'}$, and $k_0$ are a diffusion coefficient, an absorption coefficient, a reduced scattering coefficient and a magnitude of wave vector, respectively;
$q_0(r)$ is a source position wherein r is a set of spatial co-ordinates;
$<\Delta r^2(r,\tau)>$ is a mean square displacement which models Brownian motion as well as a random flow given by $6D_B\tau$ and $V^2\tau^2$, respectively;
$D_B$ is a particle diffusion coefficient in cm²/sec; and
V is a random flow with a unit of velocity;
the speckle contrast for the plurality of source positions and the plurality of detectors is computed based on the computed field autocorrelation and a second equation defined as follows:

$$K = \frac{2\beta}{T} \int_0^T g_1^2(r,\tau)\left(1 - \frac{\tau}{T}\right) d\tau$$

wherein $g_1(r,\tau) = \frac{G(r,\tau)}{G(r,0)}$ is a normalized field autocorrelation;
τ is a correlation time;
T is an exposure time of a detector array; and
β is 0.5; and
the difference value indicating the relationship between the speckle contrast corrected for shot noise and intensity gradient and the baseline speckle contrast measurement value is computed using a third equation defined as follows:

$$K_c^2 - K_{co}^2 = \frac{-4\beta}{T} \int_0^T c_v \tau^2 \left(1 - \frac{\tau}{T}\right) \frac{g_1^0(r,\tau)}{G(r,0)} \left[\int G(r', r_d, \tau) G_1^0(r', r_s, \tau) \Delta V^2 dr'\right] d\tau$$

wherein
$K_c$ is the speckle contrast corrected for shot noise and intensity gradient;
$r_s$ and $r_d$ are spatial coordinates of the plurality of source positions and the plurality of detectors, respectively;
$K_{co}$ is the baseline speckle contrast value;
$g_1^0$ and $G_1^0$ correspond to a baseline situation; and
$c_v = \tfrac{1}{3}(\mu_s k_0)^2$; and
wherein the third equation is discretized in a source-detector geometry to obtain a linear system of equations whose solution provides a flow contrast $\Delta V^2$.

5. A speckle contrast optical tomography system comprising:
a laser adapted to generate light;
a plurality of detectors arranged over a volume of a sample to be examined;
a plurality of optical fibers adapted to guide the light from the laser to a plurality of source positions;
wherein the laser has a coherence length of at least a source position-detector distance;
wherein the plurality of detectors and the plurality of source positions are arranged over a tissue volume of the sample in an arrangement that defines a plurality of source position-detector pairs adapted to examine the tissue volume;
the speckle contrast optical tomography system further including:
a processing device adapted to:
measure a speckle contrast for each of the plurality of source position-detector pairs, after the light transverses the tissue volume, both in the absence of flow and in the presence of flow, to generate speckle contrast data;
correct the speckle contrast data for shot-noise error and intensity gradients; and
construct a speckle contrast forward model for the speckle contrast optical tomography system by performing the following steps:
computing a field autocorrelation for the plurality of source positions and the plurality of detectors;
computing the speckle contrast for the plurality of source positions and the plurality of detectors;
computing a difference value defining a relationship between the speckle contrast corrected for shot noise and intensity gradients and a baseline speckle contrast measurement value; and
determining a linear system of equations having a solution that provides a flow contrast, based at least in part on the difference value.

6. The speckle contrast optical tomography system of claim 5, wherein:
the field autocorrelation for multiplicity of light sources and detectors is computed using a first equation defined as follows:

$$-\nabla \cdot D \nabla G(r,\tau) + (\mu_a + \tfrac{1}{3}(\mu_s k_0)^2 <\Delta r^2(r,\tau)>) G(r,\tau) = q_0(r) \quad (I)$$

wherein
G(r,τ) is an un-normalized field autocorrelation;
D, $\mu_a, \mu_{s'}$, and $k_0$ are a diffusion coefficient, an absorption coefficient, a reduced scattering coefficient and a magnitude of wave vector, respectively;
$q_0(r)$ is a point source wherein r is a set of spatial co-ordinates;
$<\Delta r^2(r,\tau)>$ is a mean square displacement which models Brownian motion as well as a random flow given by $6D_B\tau$ and
$V^2\tau^2$ respectively'
$D_B$ is a particle diffusion coefficient in cm²/sec; and
V is a random flow with unit of velocity;
the speckle contrast for the plurality of light sources and the plurality of detectors is computed using the computed field autocorrelation and a second equation defined as follows:

$$K = \frac{2\beta}{T} \int_0^T g_1^2(r,\tau)\left(1 - \frac{\tau}{T}\right) d\tau$$

wherein $g_1(r,\tau) = \frac{G(r,\tau)}{G(r,0)}$ is a normalized field autocorrelation;
τ is a correlation time;
T is an exposure time of a detector array; and
β is 0.5; and
the difference value indicating the relationship between the speckle contrast measurement corrected for shot noise and intensity gradient and the baseline speckle contrast value is computed using a third equation defined as follows:

$$K_c^2 - K_{co}^2 = \frac{-4\beta}{T} \int_0^T c_v \tau^2 \left(1 - \frac{\tau}{T}\right) \frac{g_1^0(r,\tau)}{G(r,0)} \left[\int G(r', r_d, \tau) G_1^0(r', r_s, \tau) \Delta V^2 dr'\right] d\tau$$

wherein
$K_c$ is the speckle contrast corrected for shot noise and intensity gradient;
$r_s$ and $r_d$ are spatial coordinates of the plurality of source positions and the plurality of detectors, respectively;
$K_{co}$ is the baseline speckle contrast value; and
$g_1^0$ and $G_1^0$ correspond to a baseline situation; and
$c_v = \frac{1}{3}(\mu_s k_0)^2$; and
wherein the third equation is discretized in a source-detector geometry to obtain a linear system of equations having a solution provides a flow contrast $\Delta V^2$.

* * * * *

UNITED STATES PATENT AND TRADEMARK OFFICE
CERTIFICATE OF CORRECTION

PATENT NO. : 9,538,926 B2
APPLICATION NO. : 14/141227
DATED : January 10, 2017
INVENTOR(S) : Turgut Durduran et al.

Page 1 of 1

It is certified that error appears in the above-identified patent and that said Letters Patent is hereby corrected as shown below:

In the Specification

Please add Government Support Paragraph at Column 1, Line 3:
This invention was made with government support under EB009233 awarded by the National Institutes of Health. The government has certain rights in the invention.

Signed and Sealed this
Seventh Day of January, 2020

Andrei Iancu
*Director of the United States Patent and Trademark Office*